(12) United States Patent
Nilsson et al.

(10) Patent No.: US 10,539,542 B2
(45) Date of Patent: Jan. 21, 2020

(54) PRESSURE TRANSIENT NORMALIZATION WITHIN A GAS DETECTOR

(71) Applicant: Honeywell International Inc., Morris Plains, NJ (US)

(72) Inventors: Andrew Nilsson, Calgary (CA); Dale Ashton, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 247 days.

(21) Appl. No.: 15/660,298

(22) Filed: Jul. 26, 2017

(65) Prior Publication Data

US 2019/0033276 A1    Jan. 31, 2019

(51) Int. Cl.
  *G01N 33/00* (2006.01)
  *F16K 17/02* (2006.01)
  *F16K 11/10* (2006.01)

(52) U.S. Cl.
  CPC .......... *G01N 33/0027* (2013.01); *F16K 11/10* (2013.01); *F16K 17/02* (2013.01)

(58) Field of Classification Search
  CPC ..... G01N 33/0027; F16K 11/10; F16K 17/02; F16K 15/16; F16K 17/19
  See application file for complete search history.

(56) References Cited

U.S. PATENT DOCUMENTS

| | | | | |
|---|---|---|---|---|
| 3,370,175 A | * | 2/1968 | Jordon | C12Q 1/18 324/99 R |
| 3,464,321 A | * | 9/1969 | Piotrowski, Jr. | F15B 11/08 137/102 |
| 3,488,649 A | * | 1/1970 | Lee | G01N 33/0027 340/632 |
| 3,586,029 A | * | 6/1971 | Evers | B64D 37/14 137/100 |
| 3,703,101 A | * | 11/1972 | Pence | A61B 5/1105 600/595 |
| 3,847,552 A | * | 11/1974 | Hobgood | G01N 33/0013 422/630 |

(Continued)

FOREIGN PATENT DOCUMENTS

| | | |
|---|---|---|
| CA | 2546331 A1 | 5/2005 |
| CN | 205330946 U | 6/2016 |
| CN | 205331090 U | 6/2016 |

*Primary Examiner* — David J Bolduc
(74) *Attorney, Agent, or Firm* — Wick Phillips Gould & Martin, LLP; Jerry C. Harris, Jr.

(57) ABSTRACT

Embodiments relate generally to systems and methods for normalizing the pressure proximate to a gas sensor within a gas detector. A rectifier assembly for use with a gas detector may comprise a flow barrier; a first valve connected to the flow barrier configured to open to normalize the pressure proximate to the gas sensor; a second valve connected to the flow barrier configured to open to allow airflow from the pump toward the gas sensor; and one or more retainer rings configured to position the first valve, second valve, and flow barrier with respect to one another, and configured to position the rectifier assembly within a cavity of the gas detector, wherein the rectifier assembly is configured to be located between a pump and at least one gas sensor of the gas detector; and wherein the rectifier assembly is configured to normalize pressure proximate to the gas sensor.

20 Claims, 6 Drawing Sheets

(56) References Cited

U.S. PATENT DOCUMENTS

| | | | | |
|---|---|---|---|---|
| 4,017,373 A * | 4/1977 | Shaw | G01N 27/4045 | 204/432 |
| 4,150,670 A * | 4/1979 | Jewett | A61M 16/104 | 128/204.22 |
| 4,725,293 A | 2/1988 | Gunderson | | |
| 5,892,160 A * | 4/1999 | Hall | G01N 1/2273 | 73/863.03 |
| 6,628,396 B1 * | 9/2003 | Gul | G01N 21/1702 | 250/343 |
| 9,329,066 B2 * | 5/2016 | Skarping | G01F 1/68 | |
| 2008/0195329 A1 * | 8/2008 | Prince | G01N 33/0062 | 702/23 |
| 2011/0005629 A1 * | 1/2011 | Ostrander | F16K 15/147 | 137/849 |
| 2013/0092260 A1 * | 4/2013 | Jilderos | F16K 17/046 | 137/505 |
| 2013/0219990 A1 * | 8/2013 | Allmendinger | G01N 33/0027 | 73/23.31 |
| 2014/0321031 A1 * | 10/2014 | Kramer | G01N 33/0032 | 361/618 |
| 2014/0326048 A1 * | 11/2014 | Jaffe | A61B 5/082 | 73/31.05 |
| 2014/0347663 A1 * | 11/2014 | Rodes | G01N 1/2273 | 356/338 |
| 2015/0041009 A1 * | 2/2015 | Gebauer | F16K 11/10 | 137/606 |
| 2015/0047415 A1 * | 2/2015 | Michalske | F02D 41/1454 | 73/23.31 |
| 2015/0089999 A1 * | 4/2015 | Szpak | F04B 39/0055 | 73/28.03 |
| 2015/0153254 A1 * | 6/2015 | Silvis | G01M 15/10 | 73/864 |
| 2015/0233881 A1 * | 8/2015 | Meerbeck | G01F 1/663 | 73/24.03 |
| 2015/0235816 A1 * | 8/2015 | Yun | H01J 37/32963 | 156/345.25 |
| 2017/0002967 A1 * | 1/2017 | Arndt | F16L 55/05 | |
| 2017/0138834 A1 * | 5/2017 | Krauss | G01N 1/2273 | |
| 2017/0248566 A1 * | 8/2017 | Yamada | G01N 33/0027 | |
| 2017/0299536 A1 * | 10/2017 | Tsuboi | G01N 27/123 | |
| 2018/0088073 A1 * | 3/2018 | Ryu | G01N 29/036 | |
| 2018/0364084 A1 * | 12/2018 | Cheng | G01F 3/22 | |

* cited by examiner

PRESSURE TRANSIENT NORMALIZATION WITHIN A GAS DETECTOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors may be carried by workers and/or located throughout a work place and may detect gases in the environment. Gas detectors may be configured to alert a user and/or supervisor when a harmful gas or level of gas is detected. Gas detectors may also be configured to communicate sensed information to a monitoring station.

SUMMARY

In an embodiment, a gas detector may comprise one or more gas sensor; a pump configured to provide airflow to the gas sensor; and a rectifier assembly located between the pump and the one or more gas sensor, configured to normalize pressure proximate to the gas sensor, wherein the rectifier assembly comprises one or more valves.

In an embodiment, a method for normalizing the pressure near a gas sensor may comprise pumping air toward the gas sensor using a pump; directing the air toward the gas sensor via a cavity located proximate to the gas sensor; positioning a rectifier assembly within the cavity; opening a first valve to allow airflow toward the gas sensor from the pump; and when the pressure within the cavity changes, opening a second valve to normalize the pressure within the cavity proximate to the gas sensor.

In an embodiment, a rectifier assembly for use with a gas detector may comprise a flow barrier; a first valve connected to the flow barrier configured to open to normalize the pressure proximate to the gas sensor; a second valve connected to the flow barrier configured to open to allow airflow from the pump toward the gas sensor; and one or more retainer rings configured to position the first valve, second valve, and flow barrier with respect to one another, and configured to position the rectifier assembly within a cavity of the gas detector, wherein the rectifier assembly is configured to be located between a pump and at least one gas sensor of the gas detector; and wherein the rectifier assembly is configured to normalize pressure proximate to the gas sensor.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
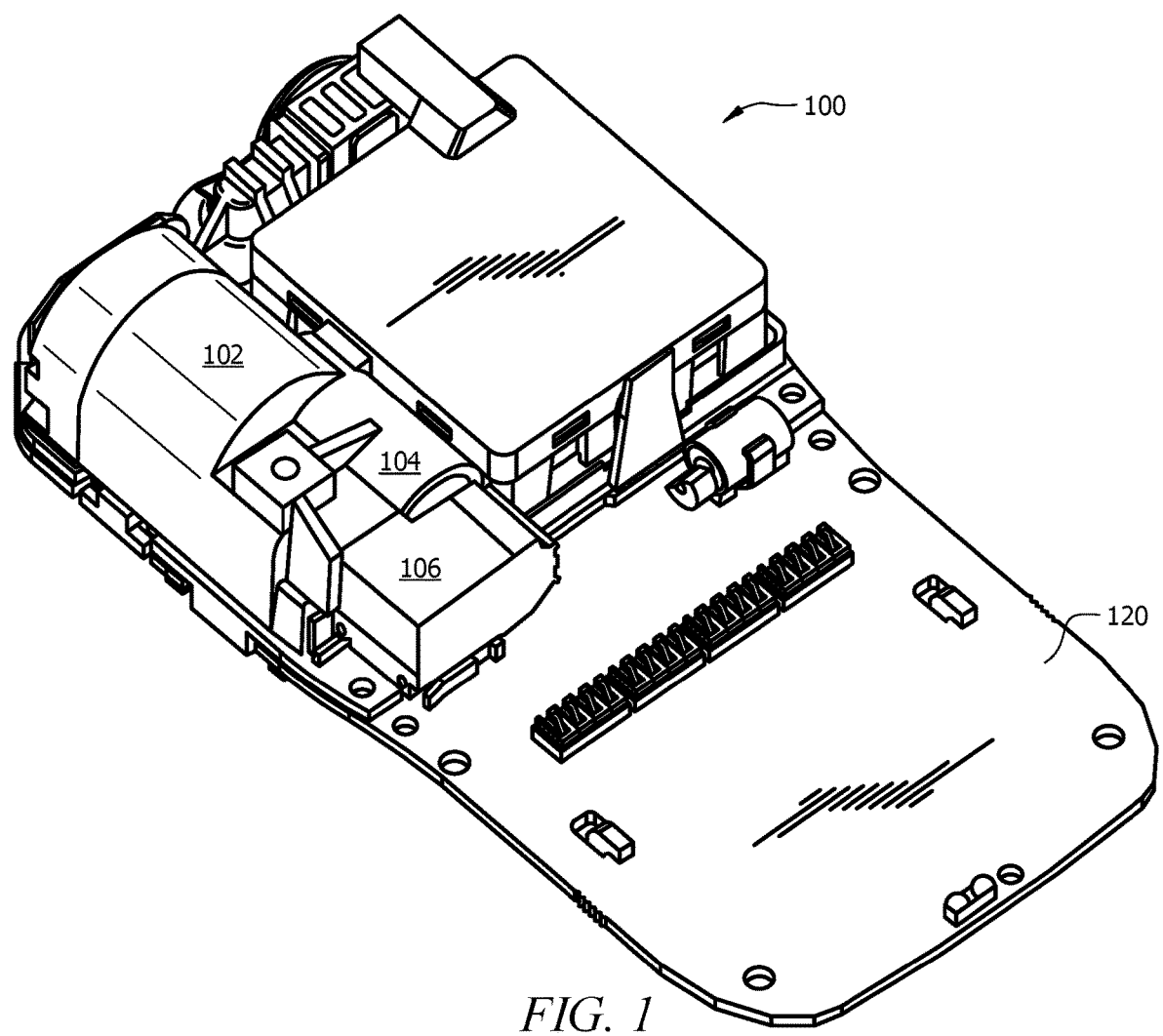
FIG. 1 illustrates a gas detector assembly according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for reducing or eliminating the effects of pressure transients within a pumped gas detector (or sensor). Certain types of gas detection sensors can be impacted by pressure transients (pulses), which may affect the readings produced by the gas sensors. Some gas detectors may commonly use a pump to draw gas (airflow) to the gas sensor for remote sampling, and pumps often generate pressure pulses (or pressure transients) due to their principles of operation, where the pressure pulses generated by the pump may affect gas detection accuracy. Complex software algorithms and electronic hardware support may be required to account for the effects of the pressure pulses, and/or extensive testing and characterization may be required to overcome this issue. Additionally, any changes in the gas sensors used within a gas detector (for example, due to manufacturing, modifications to the gas sensor design, or changing to a different gas sensor supplier) can necessitate additional testing and calibration.

Embodiments described herein comprise a rectifier assembly located within a gas detector and configured to reduce or eliminate pressure transients proximate to a gas sensor through mechanical function, which may reduce or eliminate the issues caused by pressure transients in a pumped gas detector. In a gas detector that utilizes many different types of gas sensor, the use of the rectifier assembly can eliminate the need for time spent in product testing and characterization. The rectifier assembly may remove/reduce the effort required to compensate for sensor performance changes caused by pressure transients, which may streamline and reduce risks in product development, improve product performance and predictability, and reduce software and hardware complexity within the gas detector. The simplicity of the design of the rectifier assembly may allow it to be built in a scalable form-factor, where the rectifier assembly could be quite small, improving gas sensing performance in a pumped gas detector without causing a significant increase in size.

The rectifier assembly may reduce the effects of pressure transients by placing check valves in parallel, oriented in opposing directions from one another. The valves serve to bi-directionally transfer pressure from a high-pressure side of the rectifier assembly to a low-pressure side of the rectifier assembly without causing a change to the steady-state pressure required for gas flow and without significantly impacting the gas flow path. The check valves may comprise a pair of flapper valves with travel limiting sealing faces. The pressure differential may create high and low pressure sides of the rectifier assembly, and the valves may allow pressure to equalize rapidly and reduce the amplitude of the pressure transients and smooths the pressure signal. The rectifier assembly may be located between the gas sensor and the pump supply, and may therefore reduce the overdrive effect pressure pulses can have on gas sensors.

Referring now to FIG. 1, an exemplary gas detector assembly 100 is shown, where the assembly 100 comprises a manifold 104, a gas sensor 102 located within the manifold 104, and a pump 106 configured to draw air into and/or out of the manifold 104, where the air interacts with the gas sensor 102. The assembly 100 may comprise a printed circuit board (PCB) 120 as well as other housing elements, electronic elements, sensor elements, etc.

Figure 2:
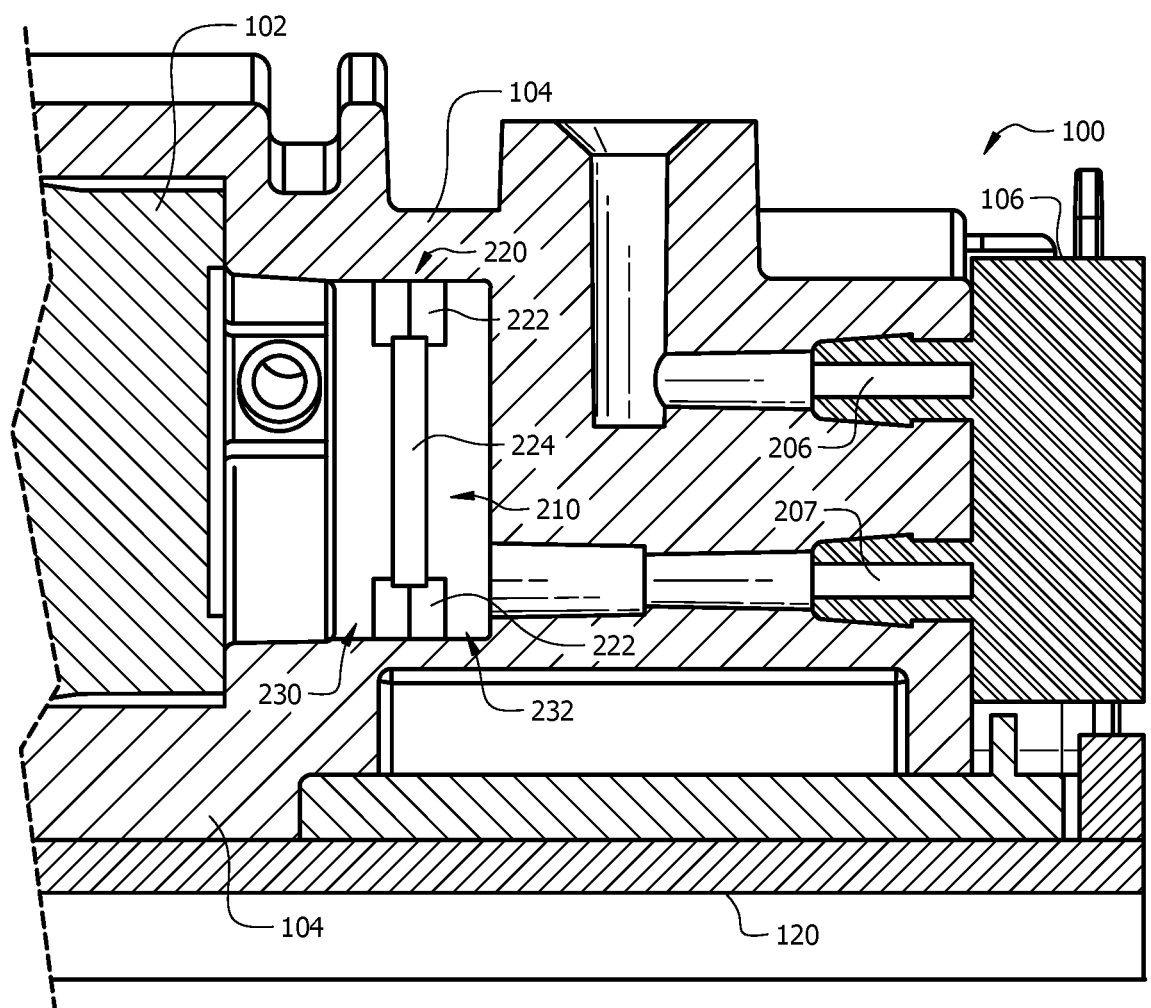
FIG. 2 illustrates a cross-sectional view of the gas detector assembly of FIG. 1, according to an embodiment of the disclosure.

Referring now to FIG. 2, a cross-sectional view illustrates the gas sensor 102 within the manifold 104, and an air inlet 206 and an air outlet 207 in fluid communication with the pump 106. The gas sensor 102 may be located near (or adjacent to) a cavity 210, wherein airflow from the pump 106 may pass through the cavity 210 toward and/or away from the gas sensor 102. In a typical assembly 100, the pressure within the cavity 210 may pulse, creating a pressure transient at or near the gas sensor 102. These pressure transients could cause irregularities in the readings of the gas sensor 102. To reduce and/or prevent the pressure transients within the cavity 210, a rectifier assembly 220 may be placed within the cavity 210. In some embodiments, the size and/or shape of the cavity 210 may be changed to accommodate the rectifier assembly 220. The position of the rectifier assembly 220 may create a first region 230 proximate to the gas sensor 102 where the pressure pulses (or transients) have been damped and a second region 232 on the opposite side of the rectifier assembly 220 where the pressure pulses (or transients) may still occur. The rectifier assembly 220 may comprise a flow barrier 224, one or more retainer rings 222, as well as one or more valve configured to allow airflow through the flow barrier 224.

Figure 3:
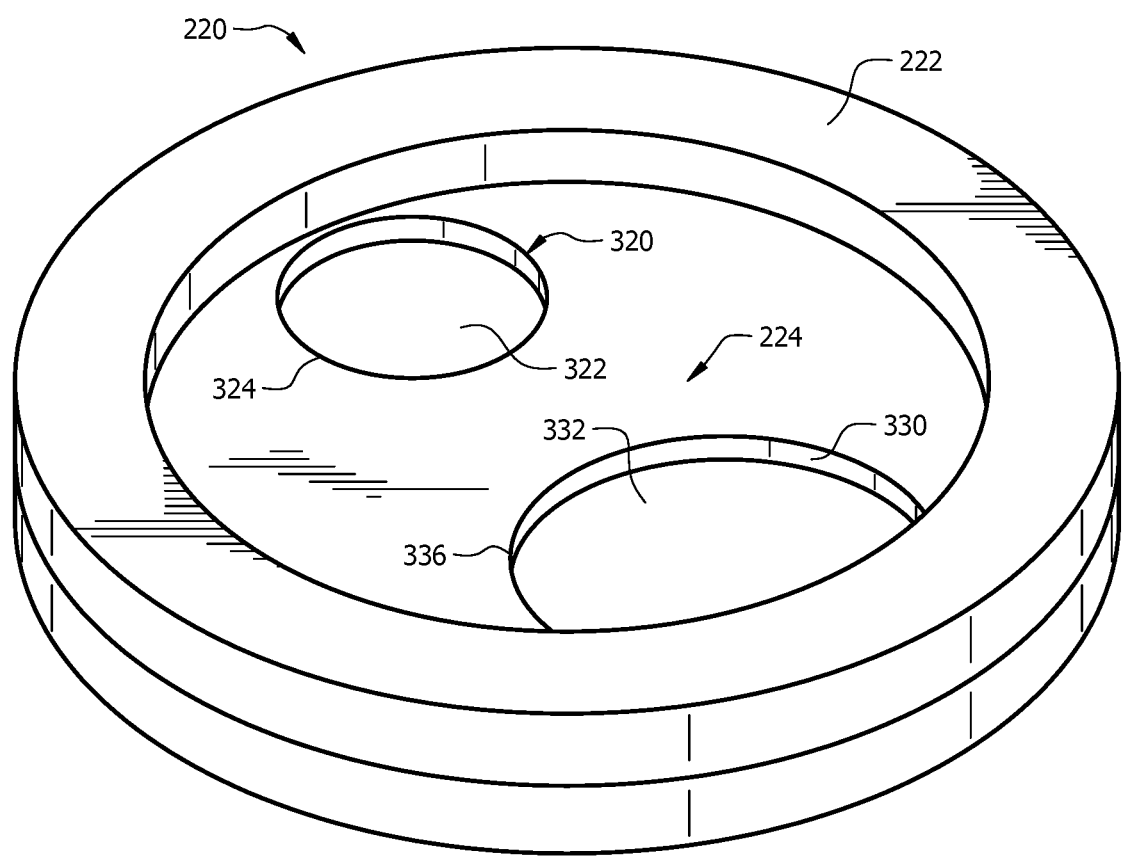
FIG. 3 illustrates a top view of a rectifier assembly according to an embodiment of the disclosure.
Figure 4:
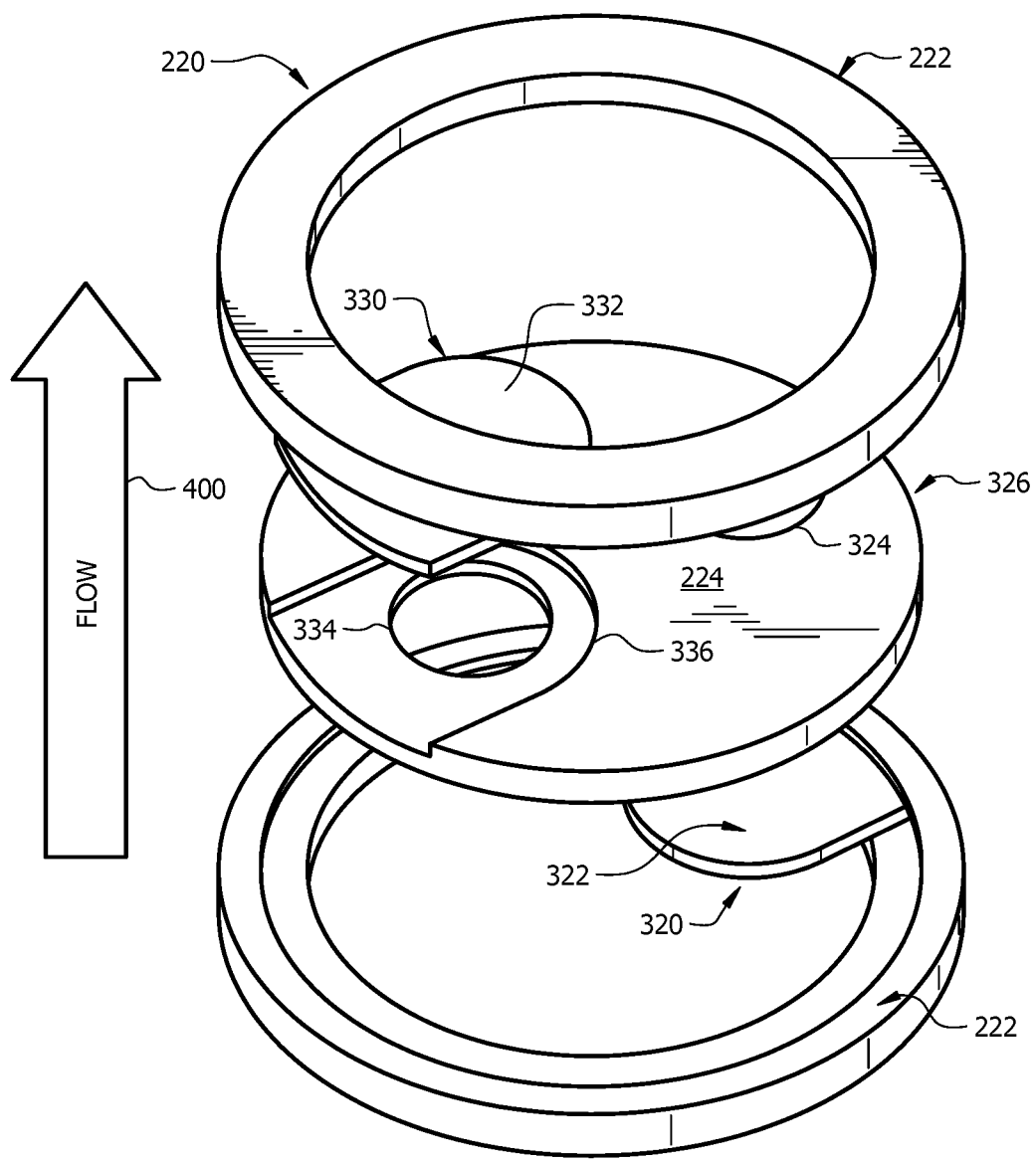
FIG. 4 illustrates an exploded view of the rectifier assembly according to an embodiment of the disclosure.
Figure 5:
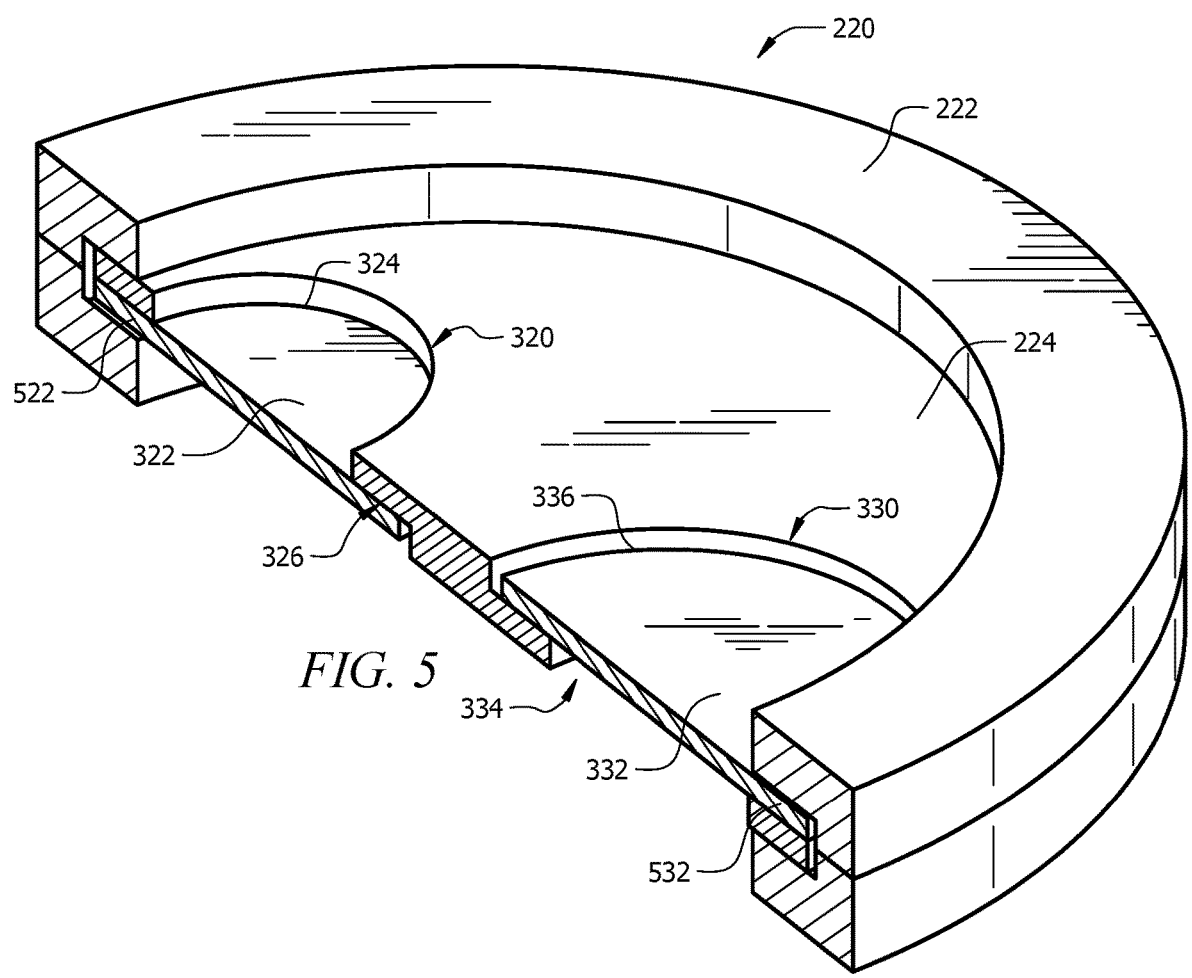
FIG. 5 illustrates a perspective, cross-sectional view of the rectifier assembly according to an embodiment of the disclosure.

The rectifier assembly 220 is shown in more detail in FIGS. 3-5. FIG. 3 illustrates a perspective view of the rectifier assembly 220. The flow barrier 224 may comprise a first valve 320 and a second valve 330, wherein the first valve 320 may be configured to move in a direction opposite the second valve 330. The first valve 320 may comprise a first opening 324, a first seat and a first flapper 322. The second valve 330 may comprise a second opening, a second seat 336, and a second flapper 332.

The rectifier assembly 220 is shown with a circular shape, but the assembly could comprise a rectangular shape, or any other shape configured to fit within the cavity 210 (shown in FIG. 2). The first flapper 322 and the second flapper 332 are shown with rounded shapes, but the flappers may comprise any shape or size, so long as they fit within the rectifier assembly. Additionally, the first flapper 322 and the second flapper 332 may be located on either side of the rectifier assembly, with respect to the gas sensor 102 (shown in FIG. 2).

Referring to FIG. 4, an exploded view of the rectifier assembly 220 is shown. As described in FIG. 3, the first valve 320 may comprise a first opening 324, a first seat 326, and a first flapper 322. The second valve 330 may comprise a second opening 334, a second seat 336, and a second flapper 332. At least a portion of the first flapper 322 and at least a portion of the second flapper 332 may be held in place against the flow barrier 224 by the retainer ring(s) 222.

When held in place, a portion of the first flapper 322 may move away from the flow barrier 224 due to pressure differences across the first valve 320, allowing airflow through the first opening 324. Additionally, the first flapper 322 may be held in place by the first seat 326 and prevented from moving in the opposite direction. When held in place, a portion of the second flapper 332 may move away from the flow barrier 224 due to pressure differences across the second valve 330, allowing airflow through the second opening 334. Additionally, the second flapper 332 may be held in place by the second seat 336 and prevented from moving in the opposite direction. The first flapper 322 and the second flapper 332 may comprise a flexible or bendable material configured to flex with respect to the retainer ring(s) 222.

As shown by the arrow 400, the airflow through the rectifier assembly may move from one side of the flow barrier to the other, via the valve(s) 320 and 330. In some embodiments, the airflow 400 may flow mainly through the second valve 330, while the first valve 320 may function to normalize the pressure within the cavity proximate to the gas sensor (as described in FIG. 2).

FIG. 5 illustrates a perspective, cross-sectional view of the rectifier assembly 220, as described above in FIGS. 3 and 4. The first valve 320 comprises the first seat 326 configured to fit around the first flapper 322, wherein the first flapper 322 covers the first opening 324. One end 522 of the first flapper 322 may be held in place by the rectifier ring(s) 222, while the remainder of the first flapper 322 may be free to move with respect to the flow barrier 224. The second valve 330 comprises the second seat 336 configured to fit around the second flapper 332, wherein the second flapper 332 covers the second opening 334. One end 532 of the second flapper 332 may be held in place by the rectifier ring(s) 222, while the remainder of the second flapper 332 may be free to move with respect to the flow barrier 224.

The mechanical properties of the first flapper 322, the second flapper 332, and the openings can affect the pressure dampening achieved by the rectifier assembly. In general, a stiffer flapper 332 may require a greater pressure differential to actuate and a smaller opening (e.g., the overall opening of in the membrane and/or the flow area between the flapper and the opening in the membrane, etc.) may present a greater resistance to fluid flow to thereby dampen the pressure peaks. The overall system can be tuned to match a pump pressure profile and/or provide a desired level of dampening. The overall dampening may take both the peak pressures as well as any sudden shocks in the pressure waves. In some embodiments, the rectifier assembly as described herein can reduce the peak pressures by at least about 50%, at least about 60%, at least about 70%, or at least about 80%.

Figure 6A:
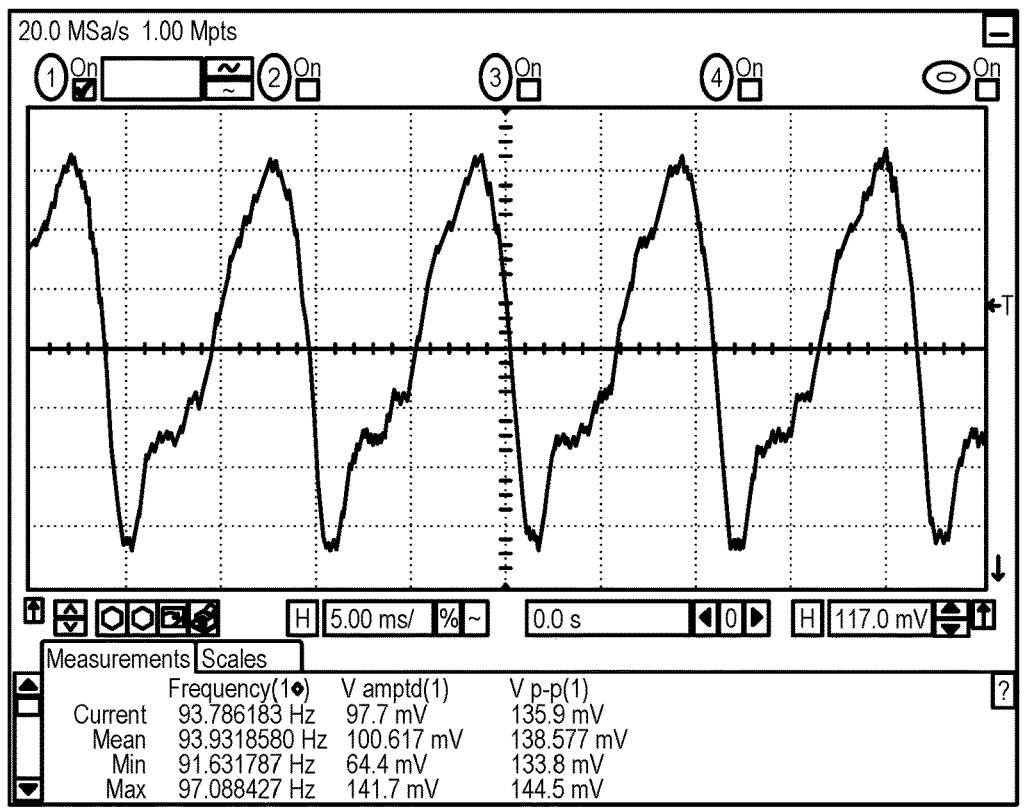
FIGS. 6A-6B illustrate readings of pressure pulses within two different gas detectors according to one or more embodiments of the disclosure.
Figure 6B:
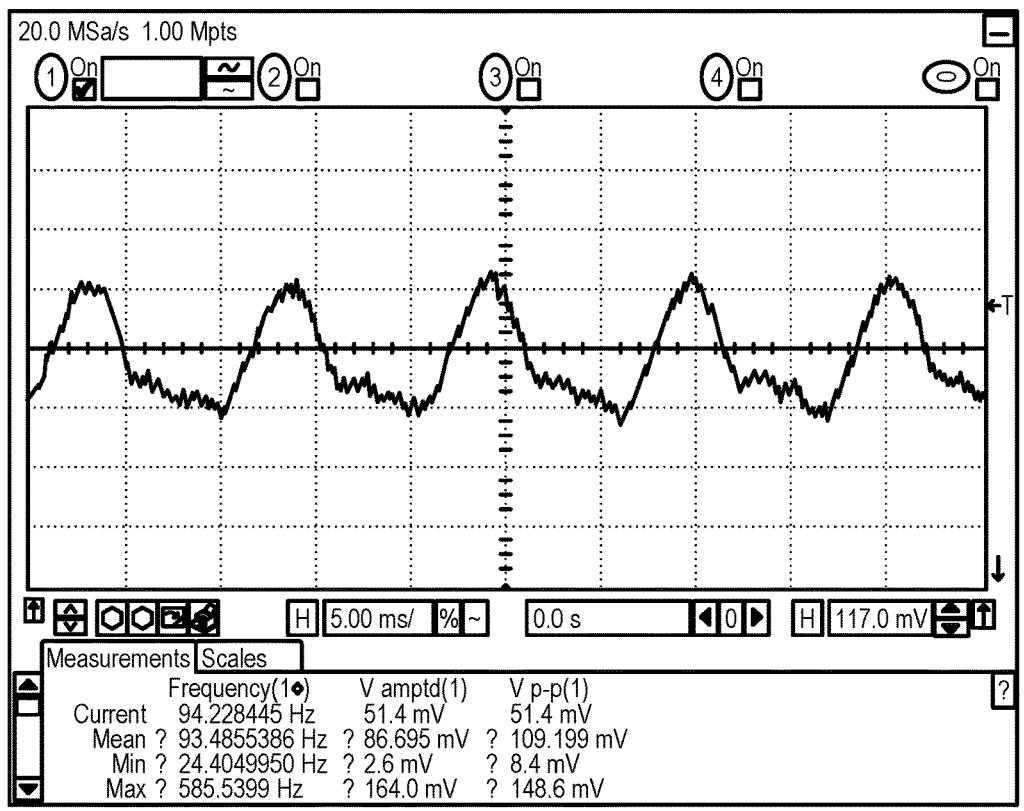

Referring to FIGS. 6A-6B, testing was completed to compare the pressure peaks in a traditional gas detector, without a rectifier assembly, (FIG. 6A) and a gas detector that includes the rectifier assembly (FIG. 6B). As shown by comparing FIG. 6A with FIG. 6B, the magnitude of the pressure pulses have been dampened (by the rectifier assembly) to approximately a third their un-dampened magnitude. In addition to reducing the amplitude of the pulses, the sudden shocks at the end of the pressure phase of the pump cycle (near-vertical falling lines in first graph) have been eliminated.

Having described various devices and methods herein, exemplary embodiments or aspects can include, but are not limited to:

In a first embodiment, a gas detector may comprise one or more gas sensor; a pump configured to provide airflow to the gas sensor; and a rectifier assembly located between the pump and the one or more gas sensor, configured to normalize pressure proximate to the gas sensor, wherein the rectifier assembly comprises one or more valves.

A second embodiment can include the gas detector of the first embodiment, wherein the rectifier assembly comprises a flow barrier; a first valve configured to open to normalize the pressure proximate to the gas sensor; a second valve configured to open to allow airflow from the pump toward the gas sensor; and one or more retainer rings configured to fit around the flow barrier, first valve, and second valve.

A third embodiment can include the gas detector of the second embodiment, wherein the first valve is located within the same plane as the second valve.

A fourth embodiment can include the gas detector of the second or third embodiments, wherein the first valve comprises a first flapper configured to move in a first direction, and wherein the second valve comprises a second flapper configured to move in a second direction.

A fifth embodiment can include the gas detector of the fourth embodiment, wherein the first valve comprises a first opening and a first seat surrounding the first opening, wherein the first flapper is positioned to fit within the first seat and to cover the first opening.

A sixth embodiment can include the gas detector of the fourth or fifth embodiments, wherein the second valve comprises a second opening and a second seat surrounding the second opening, wherein the second flapper is positioned to fit within the second seat and to cover the second opening.

A seventh embodiment can include the gas detector of any of the first to sixth embodiments, further comprising a manifold configured to contain the one or more gas sensor, the manifold defining a cavity proximate to the gas sensor, wherein the rectifier assembly is located within the cavity.

An eighth embodiment can include the gas detector of the seventh embodiment, wherein the rectifier assembly is configured to divide the cavity into a first region proximate to the gas sensor and a second region proximate to the pump.

A ninth embodiment can include the gas detector of the seventh or eighth embodiments, wherein the manifold comprises a pump outlet connected to the pump, and wherein the pump outlet is fluidly connected to the cavity defined by the manifold.

A tenth embodiment can include the gas detector of any of the seventh to ninth embodiments, wherein the rectifier assembly is shaped to fill a cross-section of the cavity formed by the manifold.

In an eleventh embodiment, a method for normalizing the pressure near a gas sensor may comprise pumping air toward the gas sensor using a pump; directing the air toward the gas sensor via a cavity located proximate to the gas sensor; positioning a rectifier assembly within the cavity; opening a first valve to allow airflow toward the gas sensor from the pump; and when the pressure within the cavity changes, opening a second valve to normalize the pressure within the cavity proximate to the gas sensor.

A twelfth embodiment can include the method of the eleventh embodiment, further comprising sensing one or more gases within the air that is pumped to the gas sensor; and indicating, by the gas sensor, that the one or more gases were sensed.

A thirteenth embodiment can include the method of the eleventh or twelfth embodiments, further comprising dividing the cavity by the rectifier assembly into a first region proximate to the gas sensor and a second region proximate to the pump.

A fourteenth embodiment can include the method of the thirteenth embodiment, wherein opening the first valve to allow airflow toward the gas sensor comprises opening the first valve to allow airflow from the second region of the cavity to the first region of the cavity.

A fifteenth embodiment can include the method of the thirteenth or fourteenth embodiments, wherein opening the second valve to normalize the pressure comprises opening the second valve to allow airflow from the first region of the cavity to the second region of the cavity.

In a sixteenth embodiment, a rectifier assembly for use with a gas detector may comprise a flow barrier; a first valve connected to the flow barrier configured to open to normalize the pressure proximate to the gas sensor; a second valve connected to the flow barrier configured to open to allow airflow from the pump toward the gas sensor; and one or more retainer rings configured to position the first valve, second valve, and flow barrier with respect to one another, and configured to position the rectifier assembly within a cavity of the gas detector, wherein the rectifier assembly is configured to be located between a pump and at least one gas sensor of the gas detector; and wherein the rectifier assembly is configured to normalize pressure proximate to the gas sensor.

A seventeenth embodiment can include the rectifier assembly of the sixteenth embodiment, wherein the first valve is located within the same plane as the second valve.

An eighteenth embodiment can include the rectifier assembly of the sixteenth or seventeenth embodiments, wherein the first valve comprises a first flapper configured to move in a first direction, and wherein the second valve comprises a second flapper configured to move in a second direction.

A nineteenth embodiment can include the rectifier assembly of the eighteenth embodiment, wherein the first valve comprises a first opening and a first seat surrounding the first opening, wherein the first flapper is positioned to fit within the first seat and to cover the first opening.

A twentieth embodiment can include the rectifier assembly of the eighteenth or nineteenth embodiments, wherein the second valve comprises a second opening and a second seat surrounding the second opening, wherein the second flapper is positioned to fit within the second seat and to cover the second opening.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector comprising:
    a gas sensor;
    a pump configured to provide airflow to the gas sensor;
    a cavity located proximate to the gas sensor and configured to direct the airflow toward the gas sensor; and
    a rectifier assembly located within the cavity, wherein the rectifier assembly is configured to normalize pressure proximate to the gas sensor, and wherein the rectifier assembly comprises:
        a first valve configured to allow the airflow toward the gas sensor from the pump; and
        a second valve configured to normalize the pressure within the cavity proximate to the gas sensor, when the pressure within the cavity changes.

2. The gas detector of claim 1, wherein the rectifier assembly comprises:
    a flow barrier; and
    one or more retainer rings configured to fit around the flow barrier, the first valve, and the second valve.

3. The gas detector of claim 2, wherein the first valve is located within the same plane as the second valve.

4. The gas detector of claim 2, wherein the first valve comprises a first flapper configured to move in a first direction, and wherein the second valve comprises a second flapper configured to move in a second direction.

5. The gas detector of claim 4, wherein the first valve comprises a first opening and a first seat surrounding the first opening, wherein the first flapper is positioned to fit within the first seat and to cover the first opening.

6. The gas detector of claim 4, wherein the second valve comprises a second opening and a second seat surrounding the second opening, wherein the second flapper is positioned to fit within the second seat and to cover the second opening.

7. The gas detector of claim 1, further comprising a manifold configured to contain the one or more gas sensor, the manifold defining the cavity proximate to the gas sensor.

8. The gas detector of claim 7, wherein the rectifier assembly is configured to divide the cavity into a first region proximate to the gas sensor and a second region proximate to the pump.

9. The gas detector of claim 7, wherein the manifold comprises a pump outlet connected to the pump, and wherein the pump outlet is fluidly connected to the cavity defined by the manifold.

10. The gas detector of claim 7, wherein the rectifier assembly is shaped to fill a cross-section of the cavity formed by the manifold.

11. A method for normalizing pressure near a gas sensor, the method comprising:
   pumping air toward the gas sensor using a pump;
   directing the air toward the gas sensor via a cavity located proximate to the gas sensor;
   opening a first valve in a rectifier assembly within the cavity to allow airflow toward the gas sensor from the pump; and
   when the pressure within the cavity changes, opening a second valve in the rectifier assembly to normalize the pressure within the cavity proximate to the gas sensor.

12. The method of claim 11, further comprising sensing one or more gases within the air that is pumped to the gas sensor; and providing an indication of a gas concentration of the one or more gases.

13. The method of claim 11, further comprising dividing the cavity with the rectifier assembly into a first region proximate to the gas sensor and a second region proximate to the pump.

14. The method of claim 13, wherein opening the first valve to allow airflow toward the gas sensor comprises opening the first valve to allow airflow from the second region of the cavity to the first region of the cavity.

15. The method of claim 13, wherein opening the second valve to normalize the pressure comprises opening the second valve to allow airflow from the first region of the cavity to the second region of the cavity.

16. A rectifier assembly for use with a gas detector, the rectifier assembly comprising:
   a flow barrier;
   a first valve connected to the flow barrier and configured to open to allow airflow from a pump of the gas detector toward a gas sensor of the gas detector;
   a second valve connected to the flow barrier and configured to open to normalize pressure within a cavity of the gas detector that is located proximate to the gas sensor, when the pressure within the cavity changes, wherein the airflow toward the gas sensor is directed via the cavity; and
   one or more retainer rings configured to position the first valve, the second valve, and the flow barrier with respect to one another, and further configured to position the rectifier assembly within the cavity of the gas detector,
   wherein the rectifier assembly is configured to be located between the pump and the at least one gas sensor of the gas detector, and
   wherein the rectifier assembly is configured to normalize the pressure proximate to the gas sensor.

17. The rectifier assembly of claim 16, wherein the first valve is located within the same plane as the second valve.

18. The rectifier assembly of claim 16, wherein the first valve comprises a first flapper configured to move in a first direction, and wherein the second valve comprises a second flapper configured to move in a second direction.

19. The rectifier assembly of claim 18, wherein the first valve comprises a first opening and a first seat surrounding the first opening, wherein the first flapper is positioned to fit within the first seat and to cover the first opening.

20. The rectifier assembly of claim 18, wherein the second valve comprises a second opening and a second seat surrounding the second opening, wherein the second flapper is positioned to fit within the second seat and to cover the second opening.

* * * * *